United States Patent [19]
Gabriel

[11] Patent Number: 6,048,336
[45] Date of Patent: Apr. 11, 2000

[54] INJECTION DEVICE

[75] Inventor: Jochen Gabriel, Stuttgart, Germany

[73] Assignee: Medico, Ascona, Switzerland

[21] Appl. No.: 09/000,596

[22] Filed: Dec. 30, 1997

[30] Foreign Application Priority Data

Mar. 3, 1997 [DE] Germany .......................... 297 03 820

[51] Int. Cl.[7] .................................................. A61M 5/24
[52] U.S. Cl. .......................................... 604/211; 604/207
[58] Field of Search ..................................... 604/207–211

[56] References Cited

U.S. PATENT DOCUMENTS

| | | | |
|---|---|---|---|
| 4,936,833 | 6/1990 | Sams ........................................ | 604/232 |
| 4,973,318 | 11/1990 | Holm et al. ............................. | 604/208 |
| 5,104,380 | 4/1992 | Holman et al. ........................ | 604/117 |
| 5,226,895 | 7/1993 | Harris ..................................... | 604/208 |
| 5,679,111 | 10/1997 | Hjertman et al. ...................... | 604/135 |

*Primary Examiner*—Corrine McDermott
*Attorney, Agent, or Firm*—Milton Oliver; Ware, Fressola, Van der Sluys & Adolphson LLP

[57] ABSTRACT

An injection device has a housing (112,116) wherein there is a longitudinally movable expressing member (186) for expressing an injection fluid from a fluid container (118). In order to displace the expressing member (186) longitudinally within the housing, an actuating member (170, 172) is associated therewith. The actuating member is displaceable between a proximal end position and a distal end position. Between the actuating member (170, 172) and the expressing member (186), a position-dependent connecting device (166", 167", 198, 210, 212) is provided, which is disabled in the distal end position of the actuating member (170, 172) and is enabled in a position range adjacent to the distal end position of the actuating member (170, 172) including its proximal end position. One thus obtains an injection device which is simple to operate, and which is especially adapted to permit a patient to repeatedly administer the same constant injection dose.

25 Claims, 17 Drawing Sheets

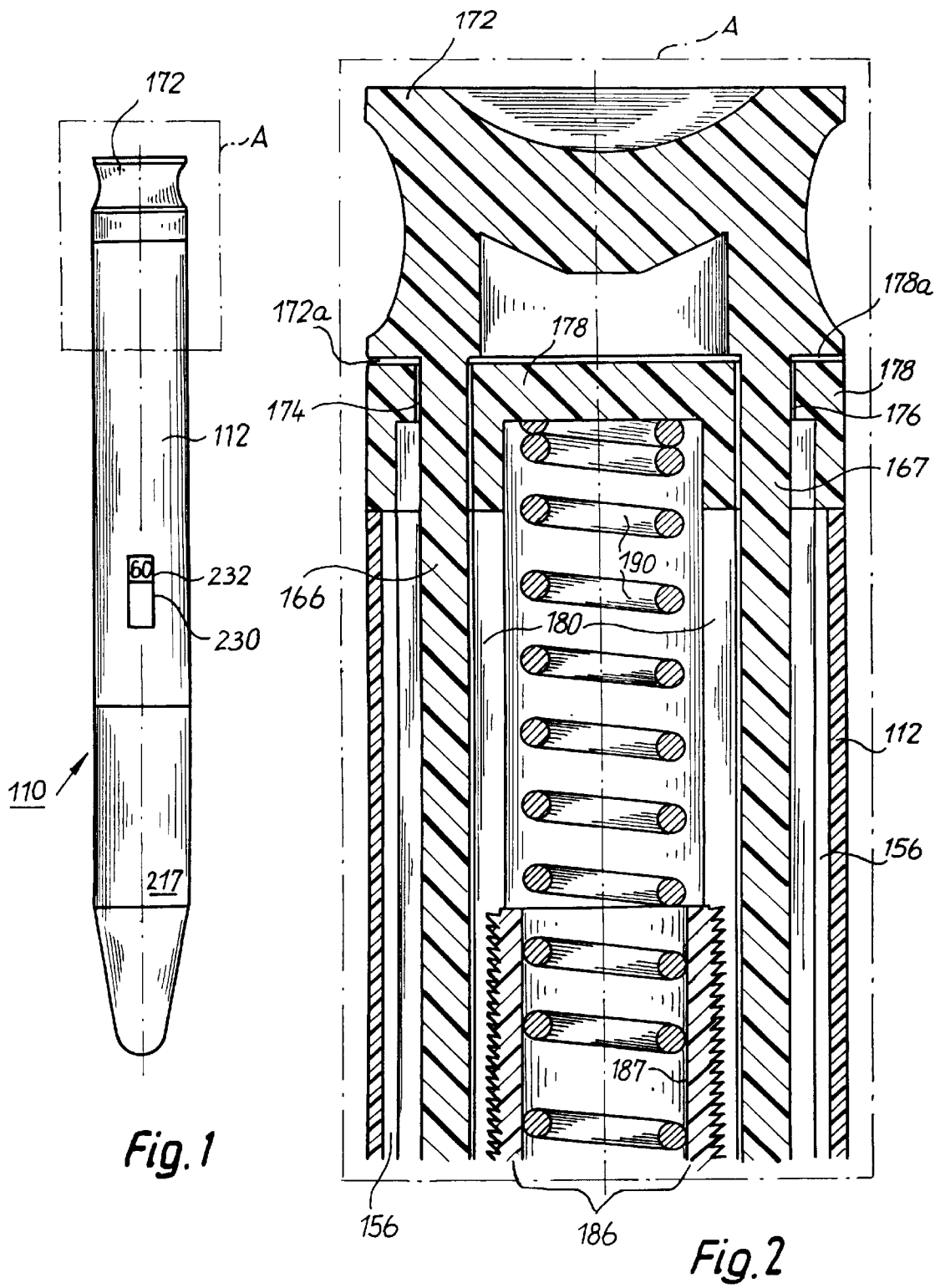

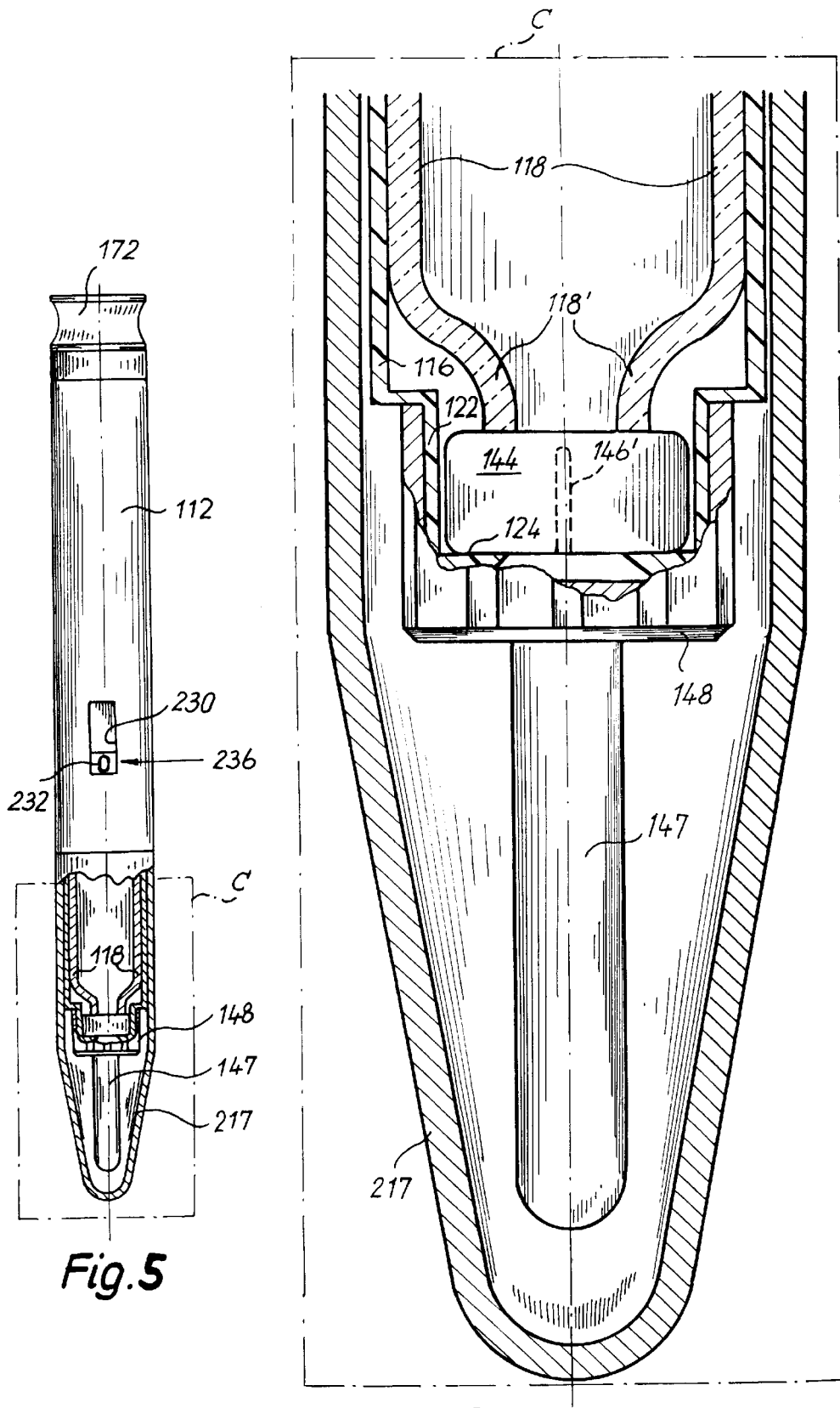

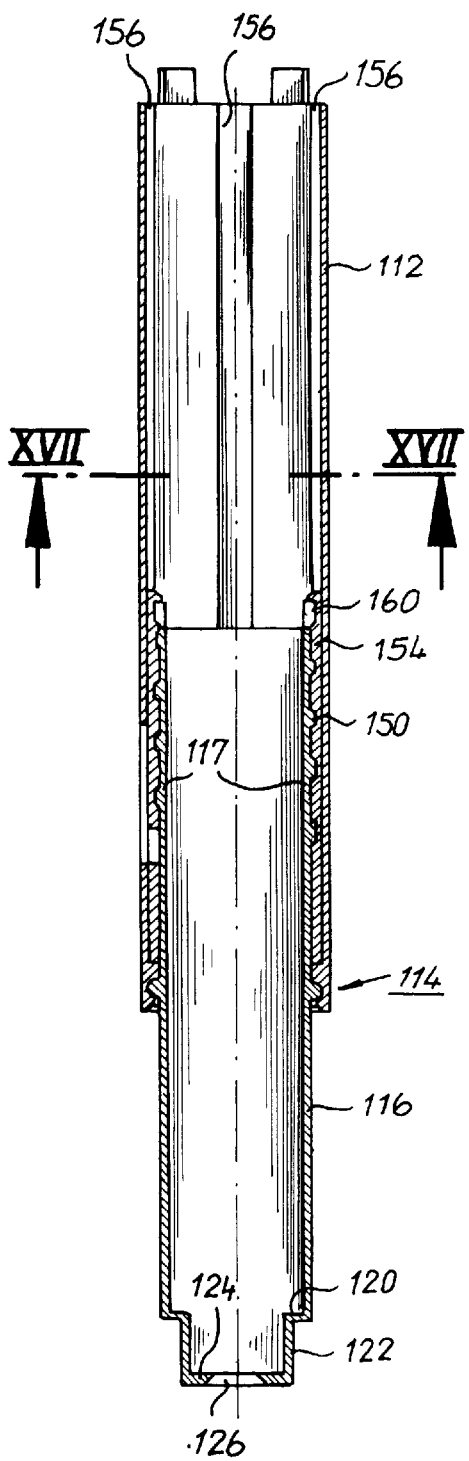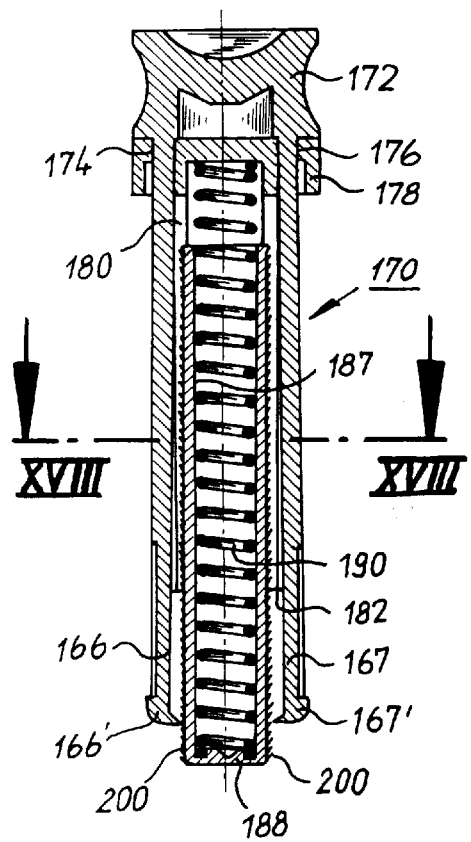
Fig. 15
Fig. 16

INJECTION DEVICE

FIELD OF THE INVENTION:

The present invention relates generally to devices for self-injection of medication and, more particularly, to a device having a housing and a longitudinally movable piston rod disposed in the housing for expression of an injectable fluid from a fluid container.

BACKGROUND

Such injection devices are used primarily by older diabetics, who often no longer see well and who can be overwhelmed by manipulation of complex devices. Therefore, the devices must be simple and as foolproof to operate as possible, so that the correct dose is always injected.

SUMMARY OF THE INVENTION

Therefore, it is an object of the invention to provide a new injection device, of the aforementioned type, which operates simply and reliably.

Briefly, this is achieved by providing in the device an expressing member, an actuating member, and a position-dependent connecting device which couples the actuating member to the expressing member to expel fluid from a container through the injection needle. Through the activation and deactivation of the connecting device in dependence upon the axial position of the actuating member relative to the housing, such a device becomes very simple to operate, substantially eliminating faulty operation.

A particularly advantageous embodiment of the invention is to bias the expressing member in the proximal direction by a force which is less than the detachment force of the plunger in the fluid container. This assures that, prior to the start of an injection, the expressing member rests reliably against the plunger of the fluid container and therefore, the full selected dose is always injected. Also, for constant dosing, it is necessary to select the injection quantity only once, and this selection will also be effective for all subsequent injections.

Further details and advantageous refinements of the invention will be apparent from the following description and accompanying drawings of several embodiments, which are to be understood as exemplary, and not as limiting the invention.

BRIEF FIGURE DESCRIPTION

FIG. 1 shows an embodiment of the injection device of the present invention, approximately actual size;

FIG. 2 is an enlarged view of detail A of FIG. 1;

FIG. 5 is a view analogous to FIGS. 1 & 3, in which the proximal portion is shown in longitudinal section;

FIG. 6 is an enlarged view of detail C of FIG. 5;

FIG. 15 is a longitudinal section through a portion of the housing of the injection device, including a rotatably mounted element in the housing for receiving a container with injectable fluid;

FIG. 16 is a longitudinal section through the expressing member and the actuating member;

DETAILED DESCRIPTION

In the following description, the expressions "proximal" and "distal" are used in the manner conventional in medicine, i.e. "proximal" meaning adjacent to the patient (the side of the injection device with the needle) and "distal" meaning remote from the patient.

Figure 3:
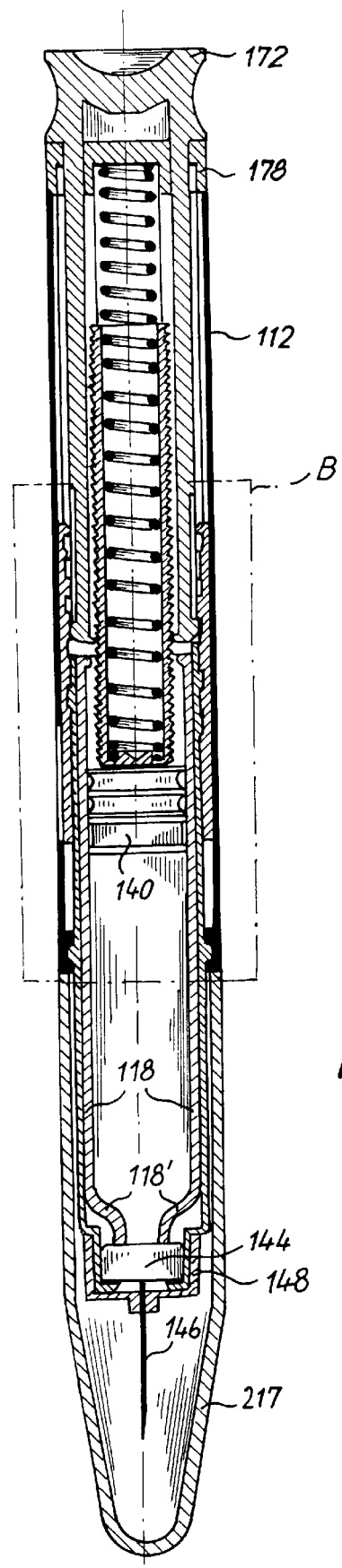
FIG. 3 is a view analogous to FIG. 1, but enlarged and in longitudinal section.
Figure 4:
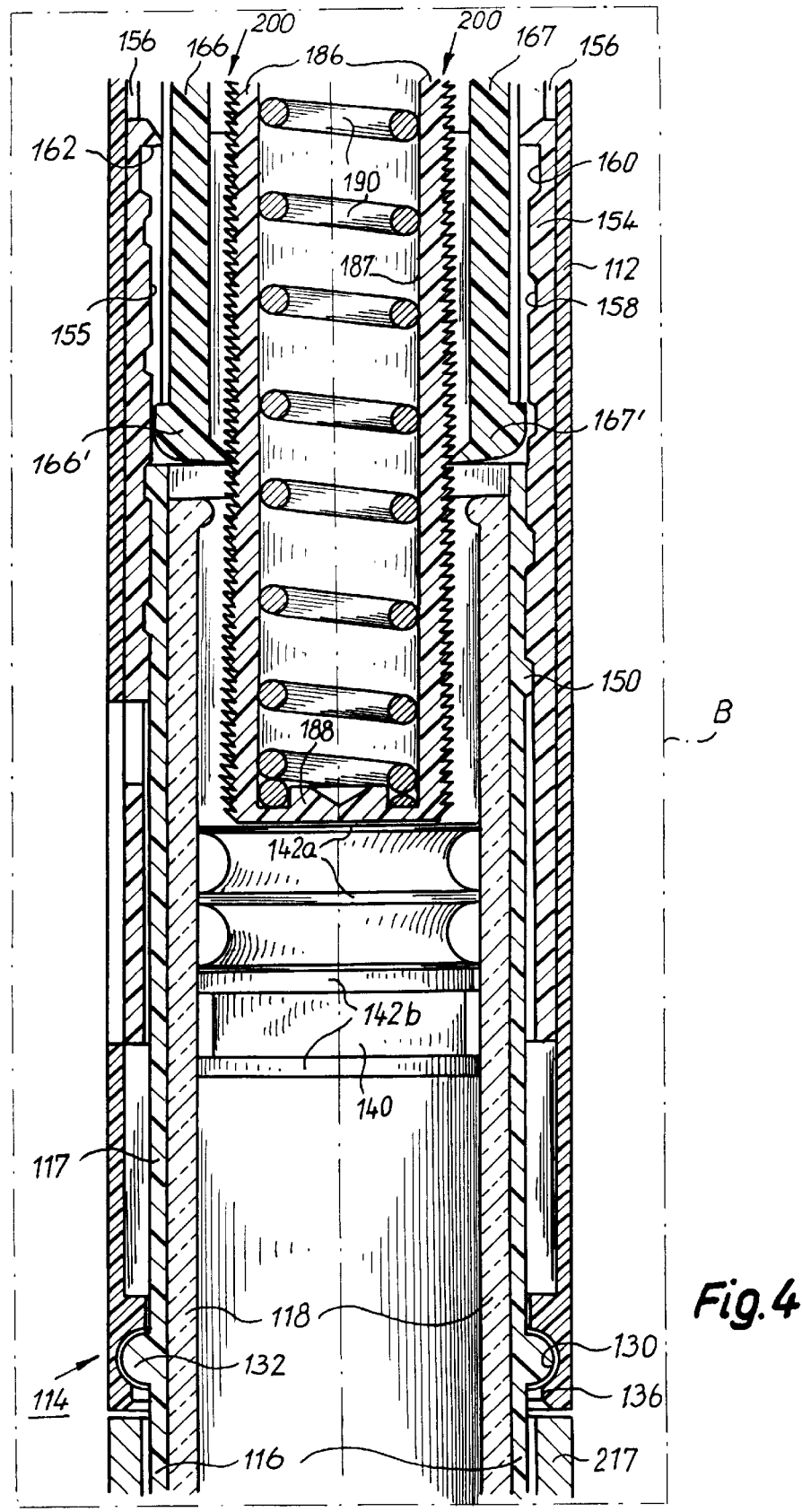
FIG. 4 is an enlarged view of detail B of FIG. 3.

As FIG. 15 shows, the housing of the injection device 110 shown in FIG. 1 has a distal section 112 in the form of a tube of a suitable plastic and, at its proximal end, a similar tubular section 116 is rotatably connected by means of a bearing 114. Section 116 serves to receive a container 118 (FIGS. 3–4) with fluid to be injected, and therefore is provided at its proximal end with a shoulder 120 (FIG. 15) and a short cylindrical section 122 of smaller diameter, which in turn has, at its proximal end, a shoulder 124 penetrated by a central opening 126. Cylindrical section 122 can be provided on its outer surface with a thread for fastening of a canula or needle carrier 148, as shown, for example in FIG. 6 or 13 together with a canula (injection needle) 146. In the unused state, as shown in FIG. 1, over the proximal end of tubular section 116, there is a protective cap 217 which serves as a sterile cover for this section and protects against soiling. The bearing 114 has, as shown in FIG. 4, an annular groove 130 at the proximal end of housing part 112, into which a complementary ridge 132 of housing section 116 clips, so that this bearing 114 serves as an axial and radial bearing. For clipping in, adjacent to annular groove 130 is a section 136 of enlarged inner diameter which widens in the proximal direction.

Figure 13:
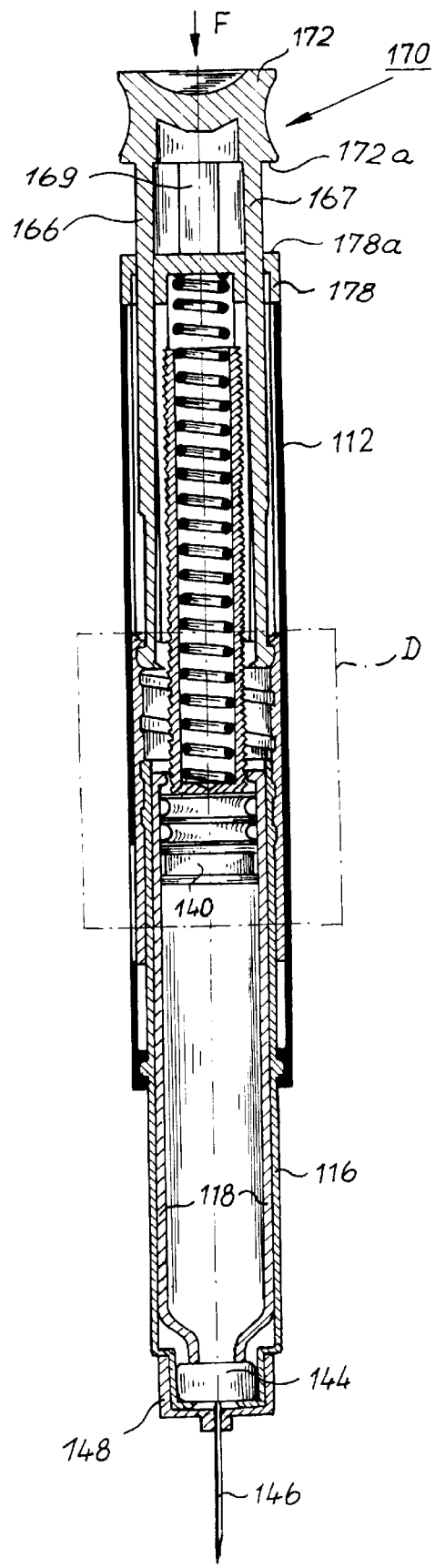
FIG. 13 is a longitudinal section through an injection device of the invention in an injection-ready configuration.

The container 118 is a so-called "cartridge" which can contain, for example, 1.5 ml or 3 ml of injectable fluid, e.g. growth hormone or insulin. It consists usually of glass, and has at its distal end a plunger 140 which can have, e.g. the form shown in FIG. 14 with multiple circumferential ribs 142a, 142b which rest with pre-tensioning against the inner surface of container 118, i.e. with corresponding friction. In order to displace plunger 140 relative to container 118, a specific minimal force is required. Only when the force on plunger 140 exceeds this value, does the plunger 140 move relative to container 118. Container 118 has, on its proximal side, a narrowed neck 118' (see FIG. 3) on which is fastened a thin rubber membrane (not shown) in the usual manner by means of a metal cap 144. The injection needle 146 shown in FIG. 13 is secured on a needle carrier 148 which can be stuck onto or screwed onto the cylindrical section 122 (FIGS. 6 & 15). Needle 146 has a distal end 146' (FIG. 6) which sticks through the above-described rubber membrane (in cap 144), so that liquid from container 118 can be pressed outward through needle 146 whenever plunger 140 in FIG.

13 is moved in the proximal direction (i.e. downward in FIG. 13). Such cartridges 118 and needles 146 are mass-produced and are familiar to those knowledgeable in this field.

As shown, e.g. in FIG. 13, the proximal housing section 116, along with the container 118 held therein, can be rotated relative to the distal housing section 112. This rotation serves for selection of an injection dose, e.g. of 4 insulin units, and this dose, once selected, remains unchanged for the subsequent injections, insofar as it is not newly set by the patient, his doctor, or his nurse. Thus, this dose is usually set only once and if, for example, four units was set once, during all subsequent injections—without new setting—a dose of four units is injected until cartridge 118 is empty.

Figure 17:
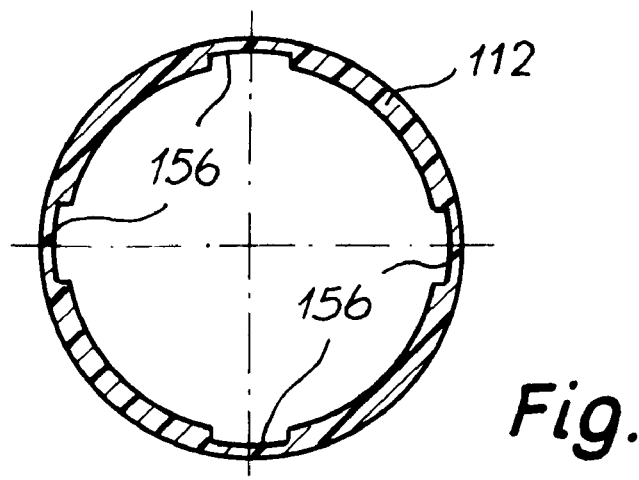
FIG. 17 is a section along line XVII—XVII of FIG. 15.

For purposes of dose setting, the proximal housing section 116 has a distal section 117 which extends into distal housing section 112 and has on its outer surface an external thread 150; see FIG. 15. The form of this thread is apparent in FIGS. 20 & 21. It is in engagement with a complementary internal thread 152 (FIG. 14) of a threaded sleeve 154, serving as a dosing element, which is guided in an axially movable manner in longitudinal grooves 156 (FIG. 17) of housing section 112, i.e. it cannot rotate relative to the latter.

If the proximal housing section 116 is rotated relative to the distal housing section 112, the dosing element 154 is moved axially relative to housing section 112. The position of dosing element 154 relative to housing section 112 thus determines the preselectable injection dose which can be adjusted to, for example, between 2 and 60 insulin units. This is explained below in greater detail, with reference to FIGS. 20 & 21.

In the region of the distal end, the cylindrical inner side 158 of dosing element 154 expands to define a groove 160 which, in the distal direction, is limited by a stop 162 (FIG. 14) in the form of an annular shoulder, and is limited in the proximal direction by a profiled shoulder 164, which can have in section the form of a circle segment, or generally: an inclined cam surface.

In practice, the groove 160 is not continuous, but rather has peripheral interruptions, in order to make manufacture as an injection-molded part easier. The groove 160 and the shoulder 162 are needed for interaction with one of the below-described clamping jaws 166 to 169.

Figure 14:
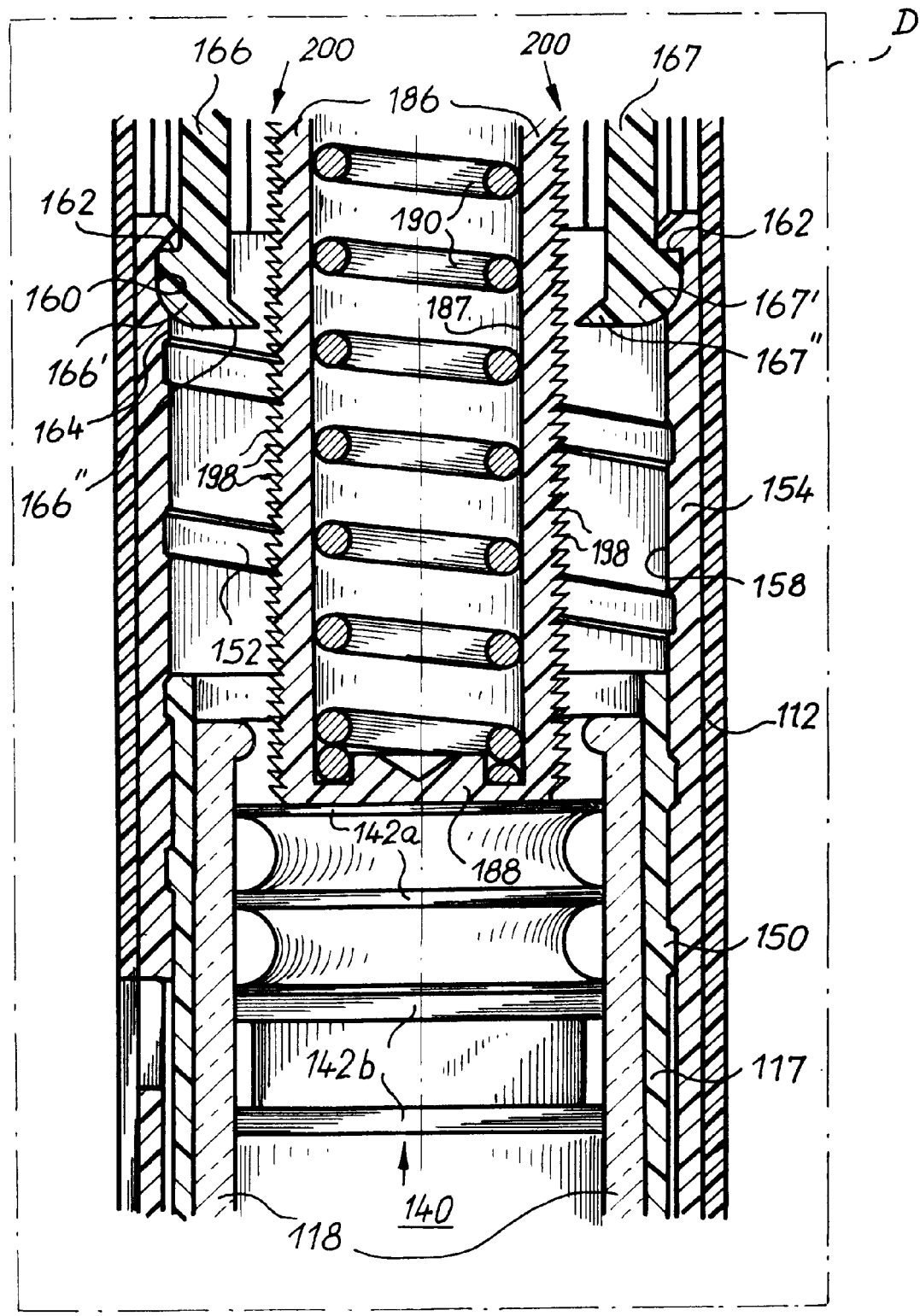
FIG. 14 is an enlarged view of detail D of FIG. 13.
Figure 18:
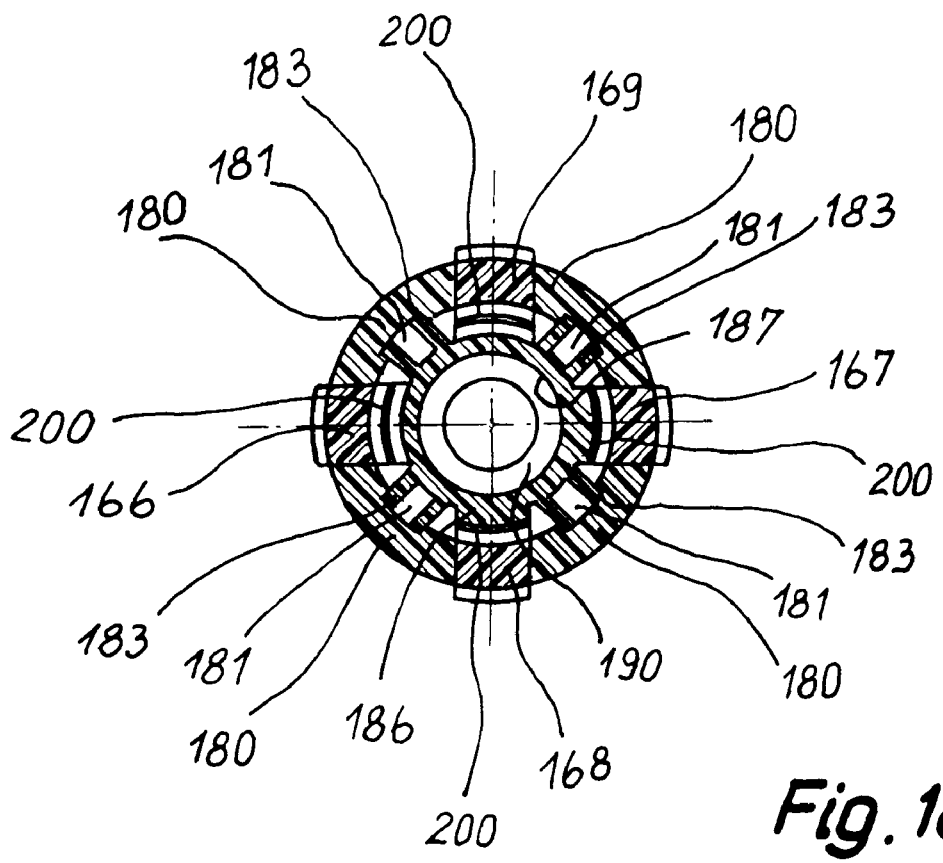
FIG. 18 is a section along line XVIII—XVIII of FIG. 16.

In the configuration shown in FIG. 13 or 14, which represents the injection device 110 prior to an injection, there rest, in this groove 160, the proximal ends of four circumferentially equally spaced clamping jaws 166, 167, 168, 169 of an actuating element 170, whose form is best apparent from FIGS. 16 and 18. These clamping jaws are integrally formed with an actuating head 172. They are guided through corresponding openings 174, 176 of an annular part 178 which forms the distal terminus of housing section 112 and are connected to the latter by, e.g. a snap-fit (see FIG. 2). In the various longitudinal sections, only the clamping jaws 166, 167 are shown. Their proximal ends are designated there by 166', 167'. Clamping jaws 166 to 169 are guided in housing section 112 in the axial direction, e.g. in the longitudinal grooves 156.

It is to be noted that it is not necessary to provide four clamping jaws 166 to 169; for example, one could equally provide three clamping jaws (not shown), displaced by 120 degrees from each other. Naturally, one would need, complementary to this, an expressing member 186 with only three racks or teeth rows 200, of which one would cooperate with each of the three clamping jaws. Preferably the forces, which the clamping jaws exert on the expressing member 186, should substantially cancel each other; i.e. if, for example, only two clamping jaws are used, these should be located opposite each other. Obviously, within the scope of the present invention, even the use of only one clamping jaw is not excluded.

Annular part 178 has on its inner side, as shown in FIG. 16, a guiding tube 180 formed with radial openings (see FIG. 18). The proximal end of tube 180 is shown in FIG. 16 at position 182. It has on its inner side four longitudinal grooves 181 and these serve for axial guidance of radial projections 183 of an essentially cylindrical hollow expressing member 186, in whose inner cylindrical cavity 187 is a compressed spring 190. The expressing member 186 might thus also be called a piston rod.

Figure 10:
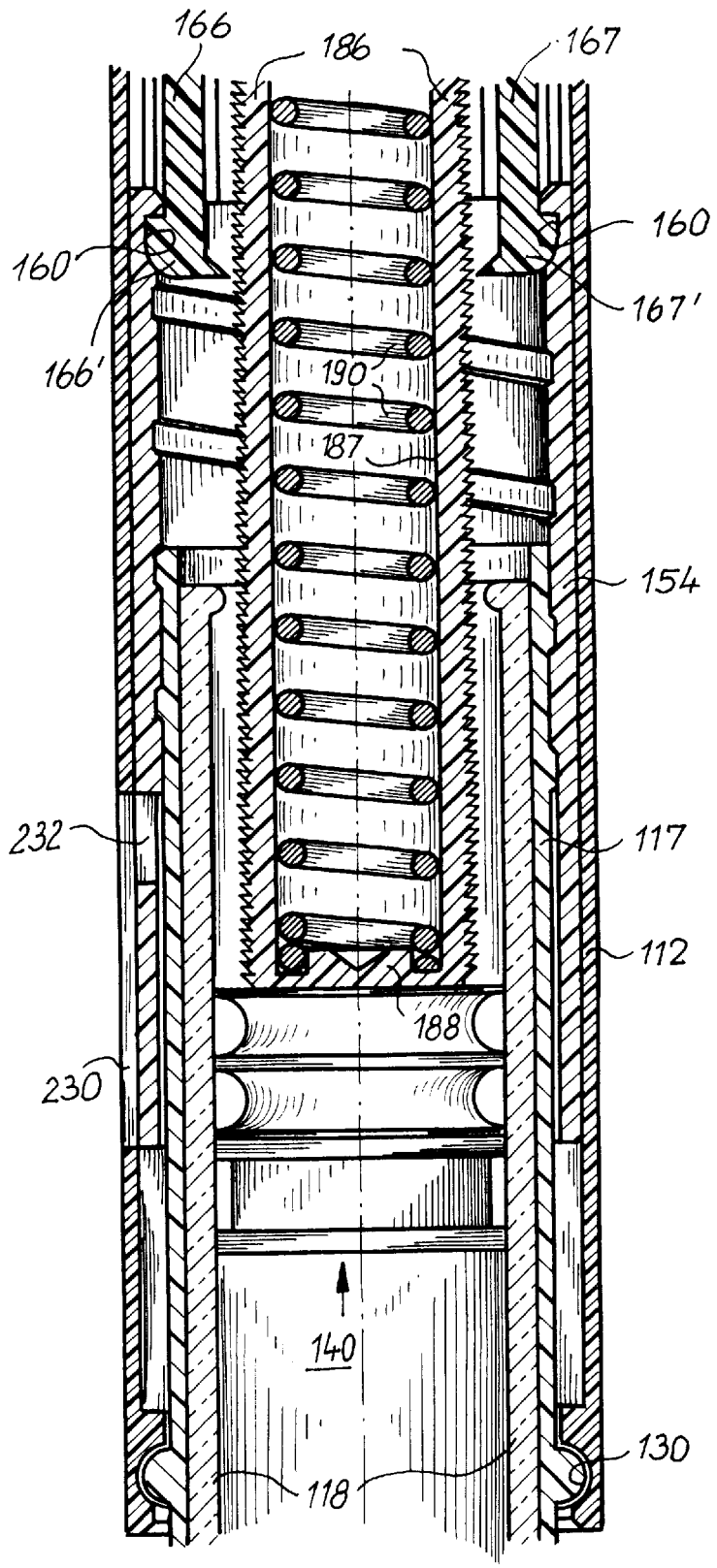
FIG. 10 shows the conclusion of preparation for an injection; the device is now ready for injection of the selected dose.

The compressed spring 190 is supported at its proximal end against a proximal floor portion 188 of expressing element 186 and, at its distal end, against annular part 178. This spring 190 has a weak bias. Its function is not, as one might perhaps believe, the support of the injection process; rather, it serves for following of the expressing element 186, so that this will always rest, as shown in FIG. 10, against plunger 140, whenever the clamping jaws 166 to 169 are not in engagement with the expressing element 186.

Figure 7:
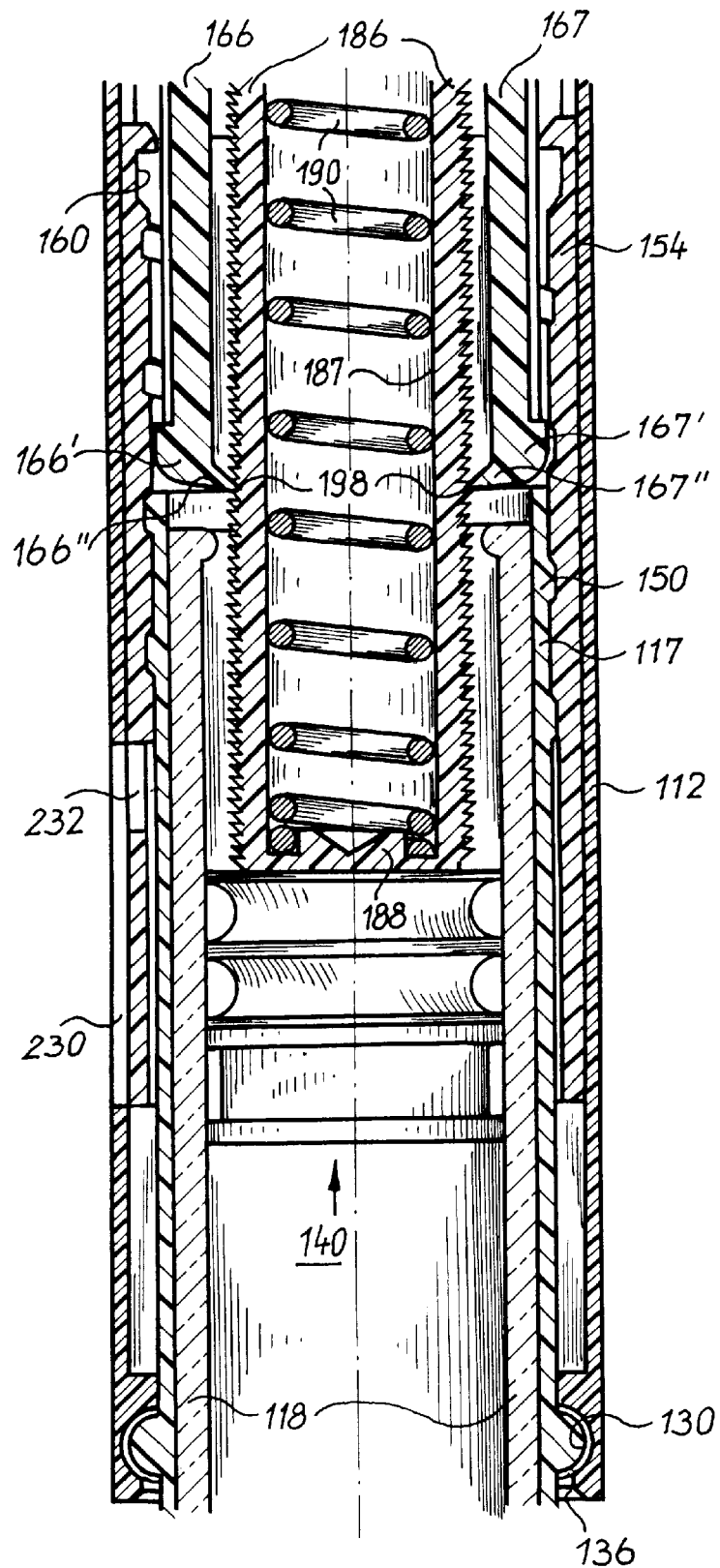
FIG. 7 is a view corresponding to FIG. 4, showing the injection device after conclusion of an injection.
Figure 12:
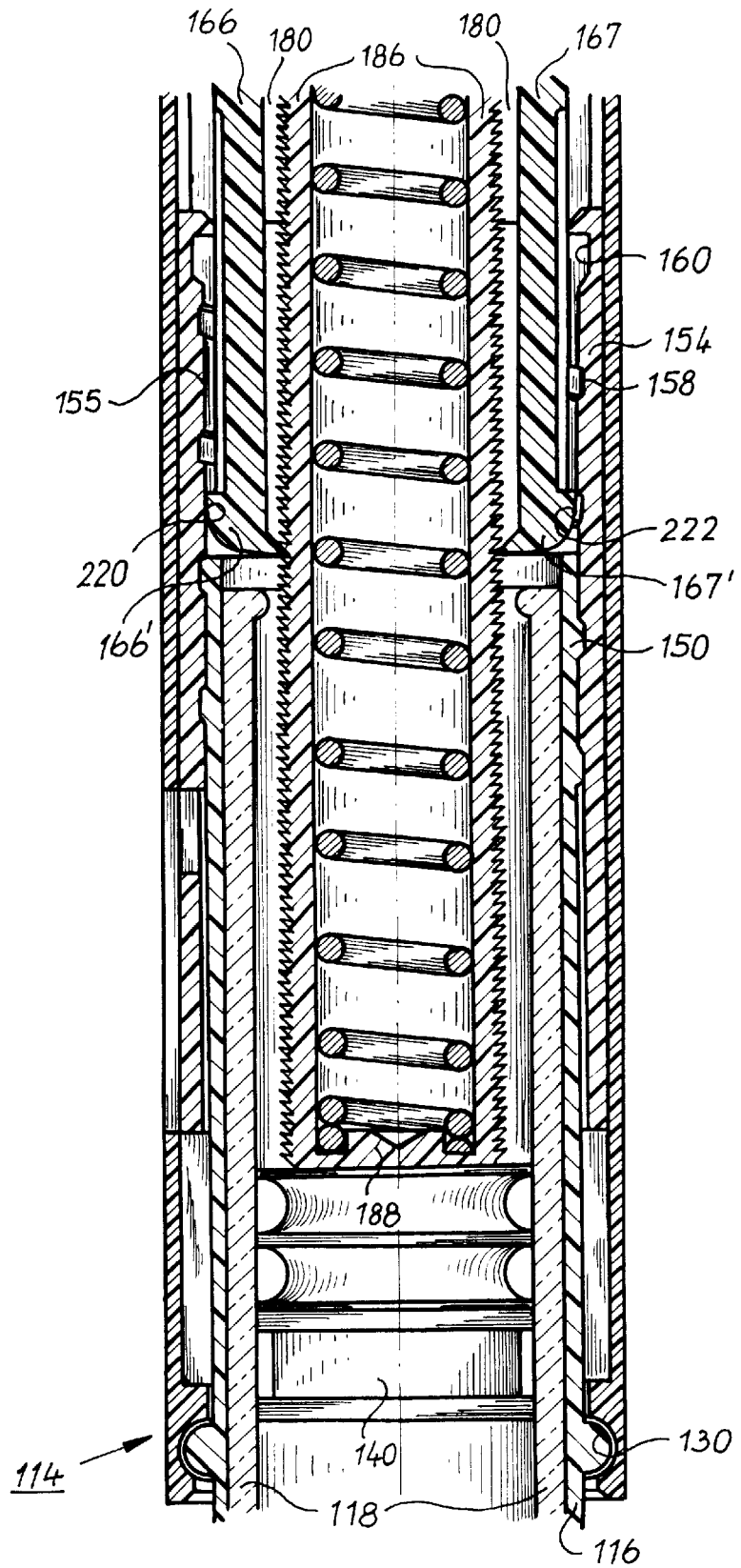
FIG. 12 shows the conclusion of an injection.

As a comparison of FIGS. 7 & 12 shows, after every injection, the plunger 140 moves further in the proximal direction, and the expressing member (piston rod) 186 must, in every position, abut with its base 188 against plunger 140 without, however, moving it, i.e. with a force whose value is less than that of a required detachment force (e.g. 2–2.5 N) of plunger 140. This means that spring 190, in its maximally compressed position, i.e. full cartridge 118, may not generate any force greater than this detachment force, and the force is advantageously smaller and in this example is maximally about 1.5 N. In other words, one could say that base 188 of the expressing member (piston rod) 186 rests with gentle pressure against plunger 140, without however being able to move it. Spring 190 thus has only a follower function and is very weak, with a low spring or elasticity constant.

As shown, for example in FIGS. 7 & 14, expressing member (piston rod) 186 has, on its outside, indentations 198 at preferably equidistant intervals, here in the form of toothing 200. The proximal ends 166', 167' of clamp jaws 166, 167 have projections 166", 167" (FIG. 14) which are formed complementary to the indentations 198. The same applies, fully analogously, to the clamp jaws 168, 169 and their associated toothings (not shown) of expressing member 186.

Clamp jaws 166 to 169 are radially outward biased, as indicated in FIG. 16, so that in the position assumed by the injector 110 directly before the injection, they are deflected radially outwardly and therefore do not engage indentations 198. FIG. 14 shows that the free ends 166', 167' are pressed, by the aforementioned bias, each into an associated groove 160 and do not engage rows of teeth 200. One thus obtains a drive connection, dependent upon the axial position of actuating member 170, 172, between clamp jaws 166–169 and the expressing member 186.

Figure 11:
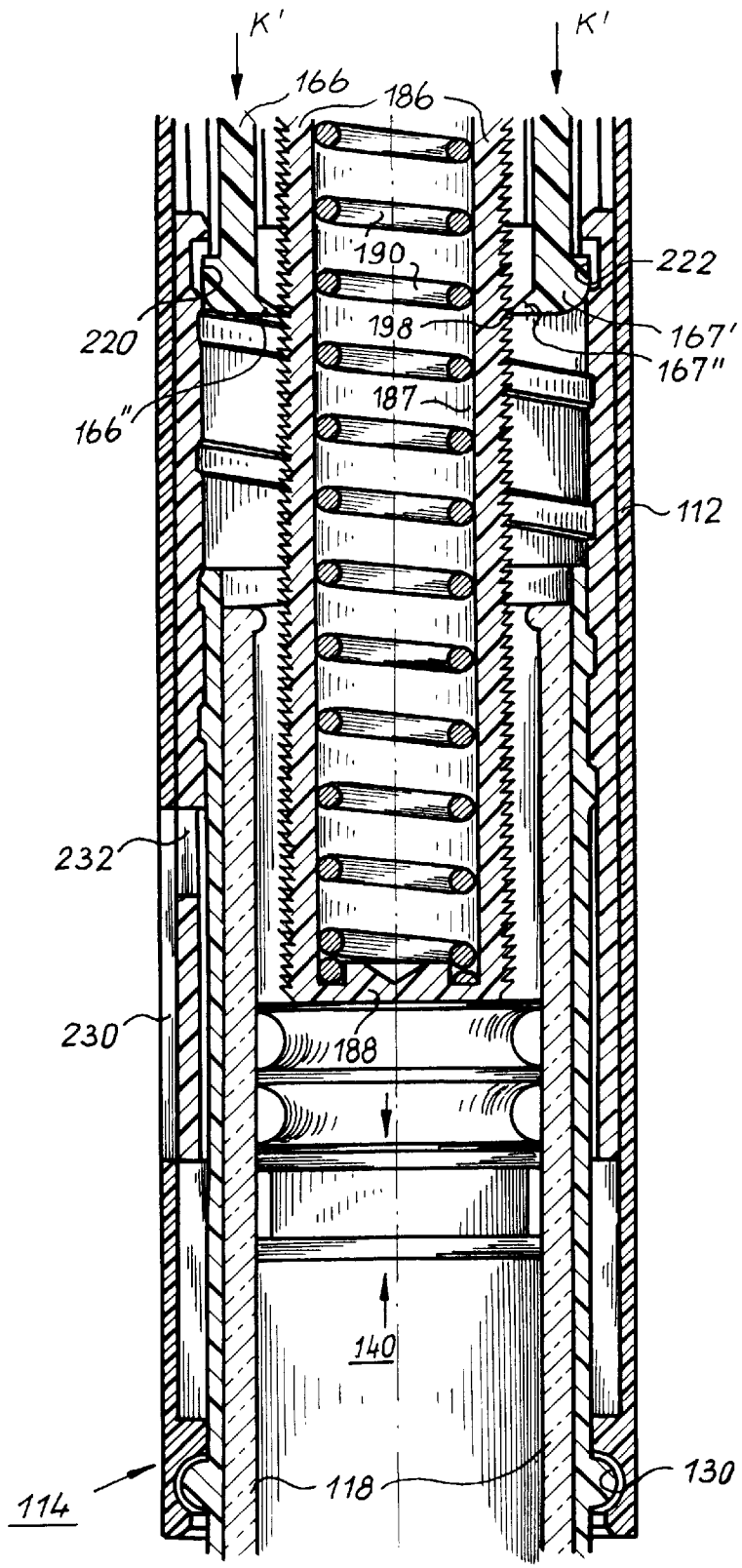
FIG. 11 shows the beginning of an injection, which occurs manually (force K')

If, as shown in FIGS. 13–14, a force F on actuating head 172 displaces it in the proximal direction, the proximal ends 166', 167' of the clamp jaws are pressed radially inward by the cam surface 164 of groove 160 and complementary form of ends 166', 167' as shown in FIG. 11 and end up with their projections 166", 167" in engagement with the respective indentations opposite the respective projection, so that, between the actuating member 170, 172 and the expressing member or piston rod 186, a drive connection is enabled, which connection was disabled in the position shown in FIGS. 13–14.

This drive connection has the effect that the movement of actuating member 170, 172 in the proximal direction (by the force F of FIG. 13) is directly transmitted to expressing member (piston rod) 186 and displaces it in the proximal direction. Since, due to the force of weak spring 190, piston rod 186 already rests with its base 188 directly against plunger 140, this movement is also directly transmitted to plunger 140, causing fluid in the preselected dosage to be expressed from container 118 via needle 146, to the extent that the actuating head 172 is displaced so far (by force F) that its proximal face 172a (FIG. 13) abuts against the distal outer face 178a of annular part 178, i.e. until the stop is reached.

Here, it is to be noted that, during this injection process and as shown in FIG. 12, each of the radially outer sides 220, 222 of proximal ends 166', 167' is pressed, by the inner side 155 of dosing element 154 in the manner of a cam control, radially inward and into engagement with the expressing member (piston rod) 186 so that, after leaving groove 160, the drive connection between actuating member 170 and expressing member 186 is constantly maintained or enabled. Preferably, this drive connection is a form-locking one, but a force-locking one would also be possible, as is readily apparent to those skilled in the art. Alternatively, this connection could be created otherwise, e.g. by excitation of a solenoid.

Mode of Operation

FIG. 7 shows the injection device after an injection. The projections 166'', 167'' of actuating member 170 stand in forced engagement with corresponding indentations 198 of tooth rows 200.

Figure 8:
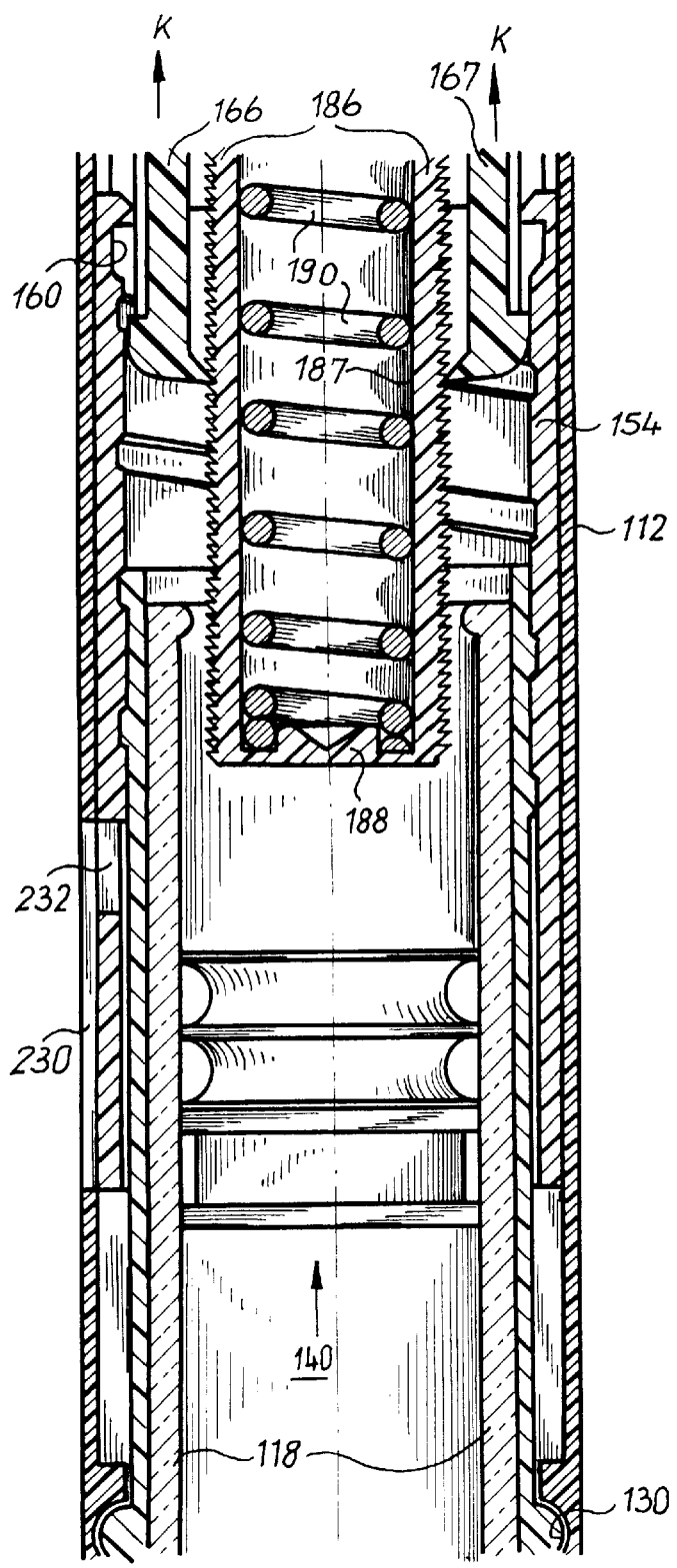
FIG. 8 shows the beginning of preparation for a subsequent injection.

According to FIG. 8, the user pulls on actuating member 170, and moves actuating head 172 with a force K in the distal direction. FIG. 8 shows an intermediate position during this movement process, and FIG. 9 shows a further progressive intermediate position, in which the projections 166', 167' have almost reached groove 160.

In FIG. 10, groove 160 has been reached. Clamp jaws 166–169 spring radially outward into this groove 160 and thereby disable the drive connection to expressing member (piston rod) 186, so that the latter promptly moves, under the influence of (weak) spring 190, in the proximal direction, until its base 188 abuts, with a light force, against plunger 140. This is the already-described follower movement of expressing member 186, and the injection device is injection-ready in this position.

Figure 9:
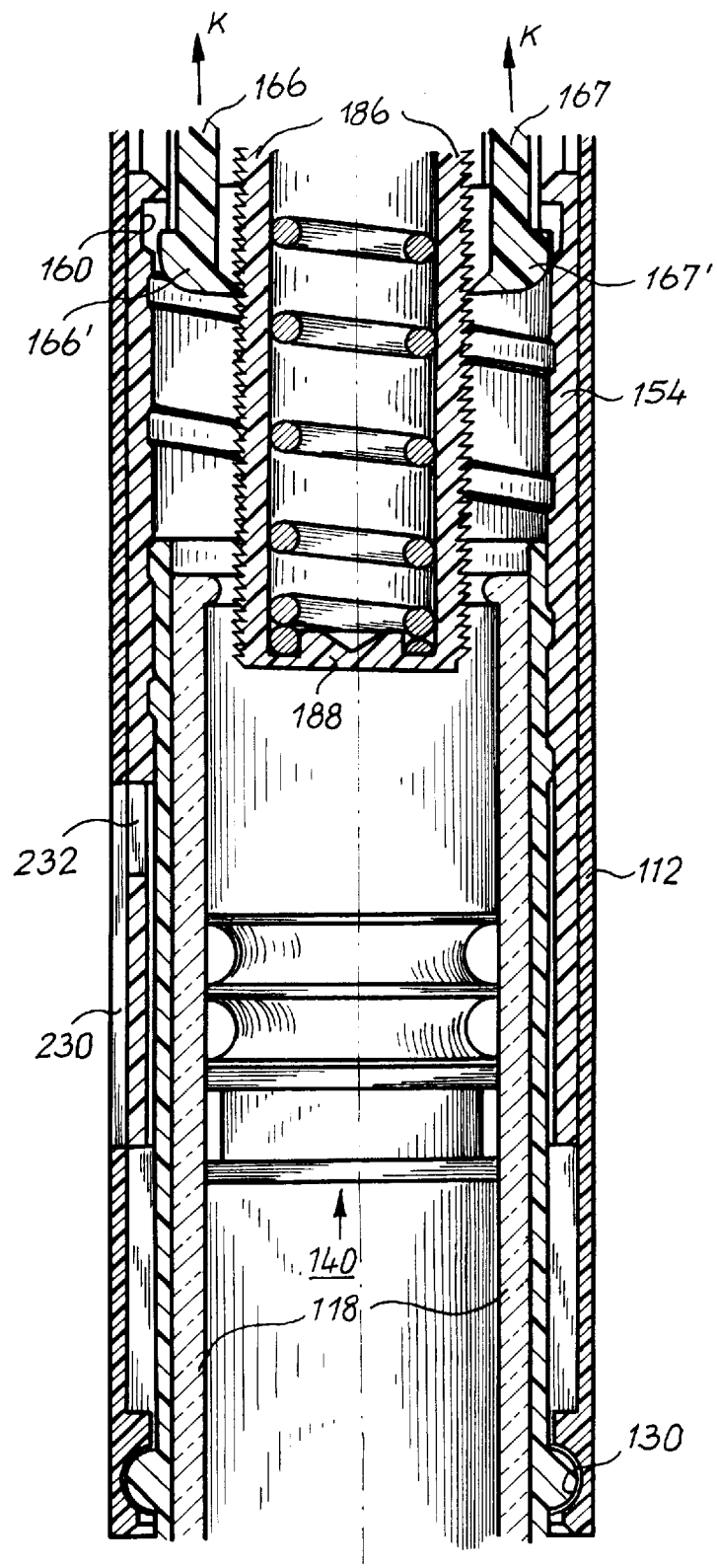
FIG. 9 shows the further progress of such preparation.

If the user interrupts the above-described process in the position of FIG. 8 or FIG. 9, spring 190 moves expressing member 186 and actuating member 170 back into the position of FIG. 7, so that in this case, no injection is possible. Rather, an injection first becomes possible when the position of FIG. 10 is reached, in which the dose, previously set by turning of housing section 116, is activated. This represents a valuable security feature and prevents the patient from injecting himself with less than the predetermined dose.

For an injection, the patient first sticks the needle 146 (FIG. 13) into his subcutaneous fat layer, and then presses with force F on the actuating head 172. Then the ends 166' 167' of clamp jaws 166–169 move radially inward and come into engagement with the respective indentations 198 opposite them. Thereby, the force F is transmitted to expressing member 186 and from it to plunger 140, so that the selected dose is expressed from container 118 and injected.

FIG. 12 shows the conclusion of this process, i.e. the end of an injection with the selected dose. As previously described, the end is reached when in FIG. 13 the annular shoulder 172a abuts against distal end face 178a of housing section 112.

Subsequent to the injection, the patient pulls the needle 146 out of the subcutaneous fat layer and replaces it with a new, sterile needle, which usually is covered with a sterile cap 147 as shown in FIGS. 5 & 6.

Figure 19:
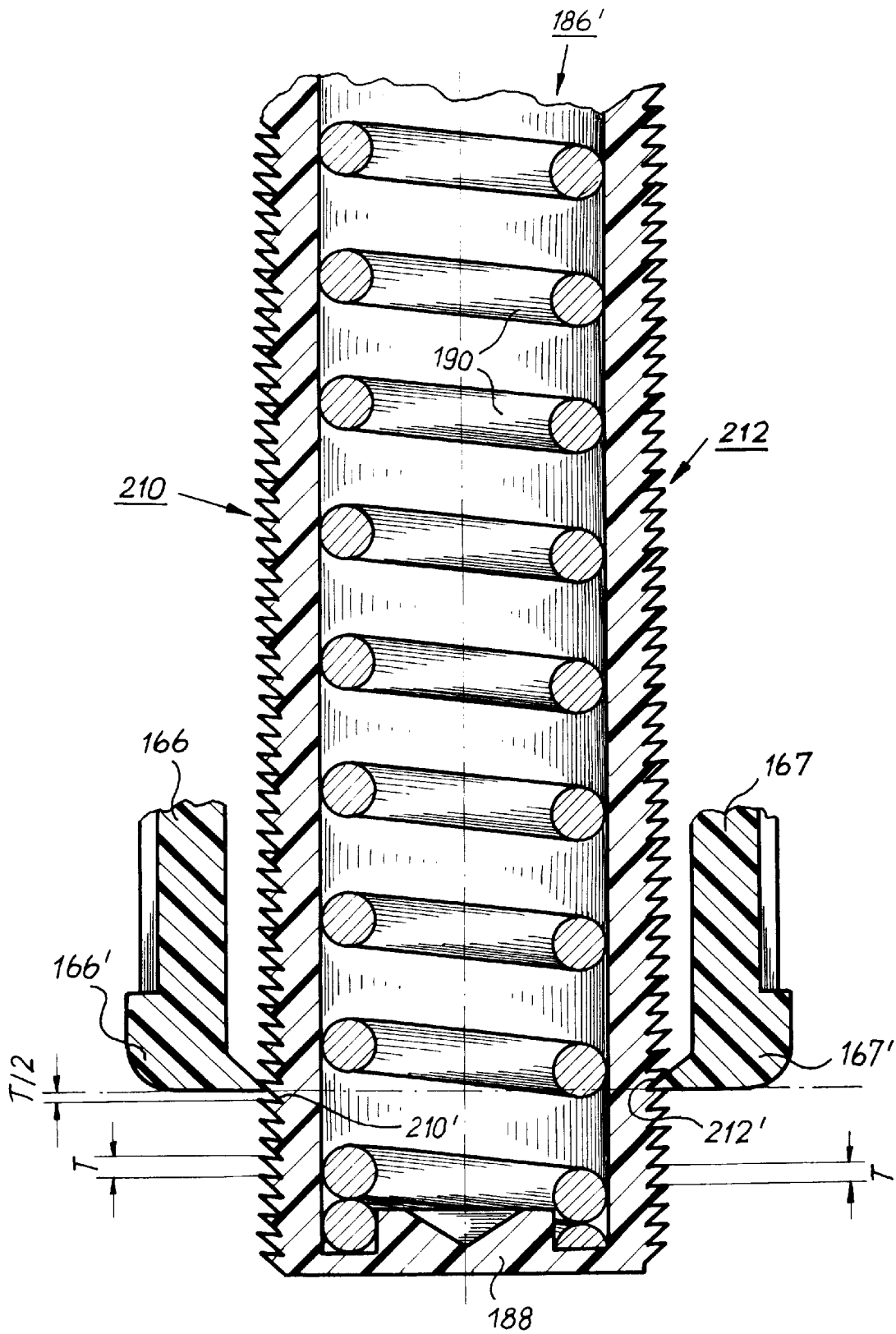
FIG. 19 is a view explaining a preferred further development of the invention.

FIG. 19 illustrates a significant improvement, which permits finer dosing. The expressing member 186' here has a left tooth row 210 and a right tooth row 212. Both have an identical tooth pitch T, but the tooth rows 210, 212 are staggered or offset with respect to each other in the axial direction by half a tooth pitch, i.e. by T/2 as shown in FIG. 19. Since clamp jaws 166, 167 oppose each other without axial displacement, clamp jaw 167, for example, would completely engage with its free end 167' into a depression 212' of tooth row 212, while the free end 166' of clamp jaw 166 would, as illustrated, engage only halfway into the associated recess 210' of tooth row 210, i.e. in the case shown, the right clamp jaw 167 is effective and provides the drive connection. Conversely, it can be that the free end 166' of clamp jaw 166 fully engages in an associated recess 210', while the free end 167' only half engages in an associated recess 212'. It is to be noted that FIG. 18 shows an analogous displacement of tooth rows 200 in section, as is readily apparent to those skilled in the art.

By this staggering or displacement, dose setting in gradations of half the tooth pitch (T/2) is possible, i.e. the dosage can in this variant be adjusted in smaller steps without requiring smaller teeth 210, 212. The tooth rows 210, 212 are shown in FIG. 19 greatly enlarged, for ease of illustration.

As one can readily recognize, one could also use, for example, three different tooth rows and stagger each relative to the others by T/3, in order to obtain still finer adjustment possibilities. Equally, it is possible to stagger or displace the free ends 166', 167' of the clamp jaws 166, 167 relative to each other, e.g. by T/2, and not stagger tooth rows 210, 212. Such and other variants will be readily available to those skilled in the art.

Figure 20:
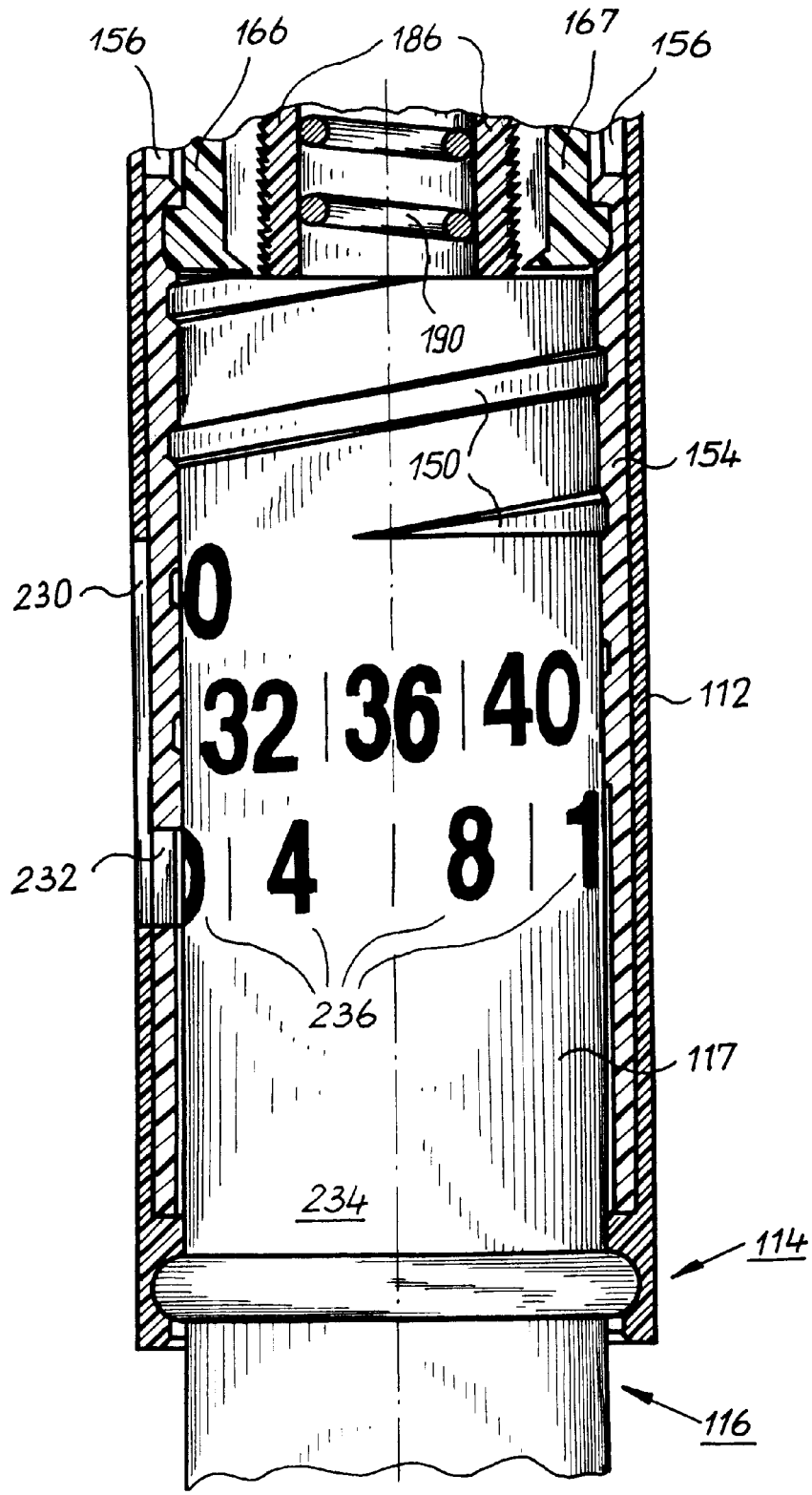
FIG. 20 is a view of the elements for dose-setting and dose-indication, specifically showing a "zero" dose selected.
Figure 21:
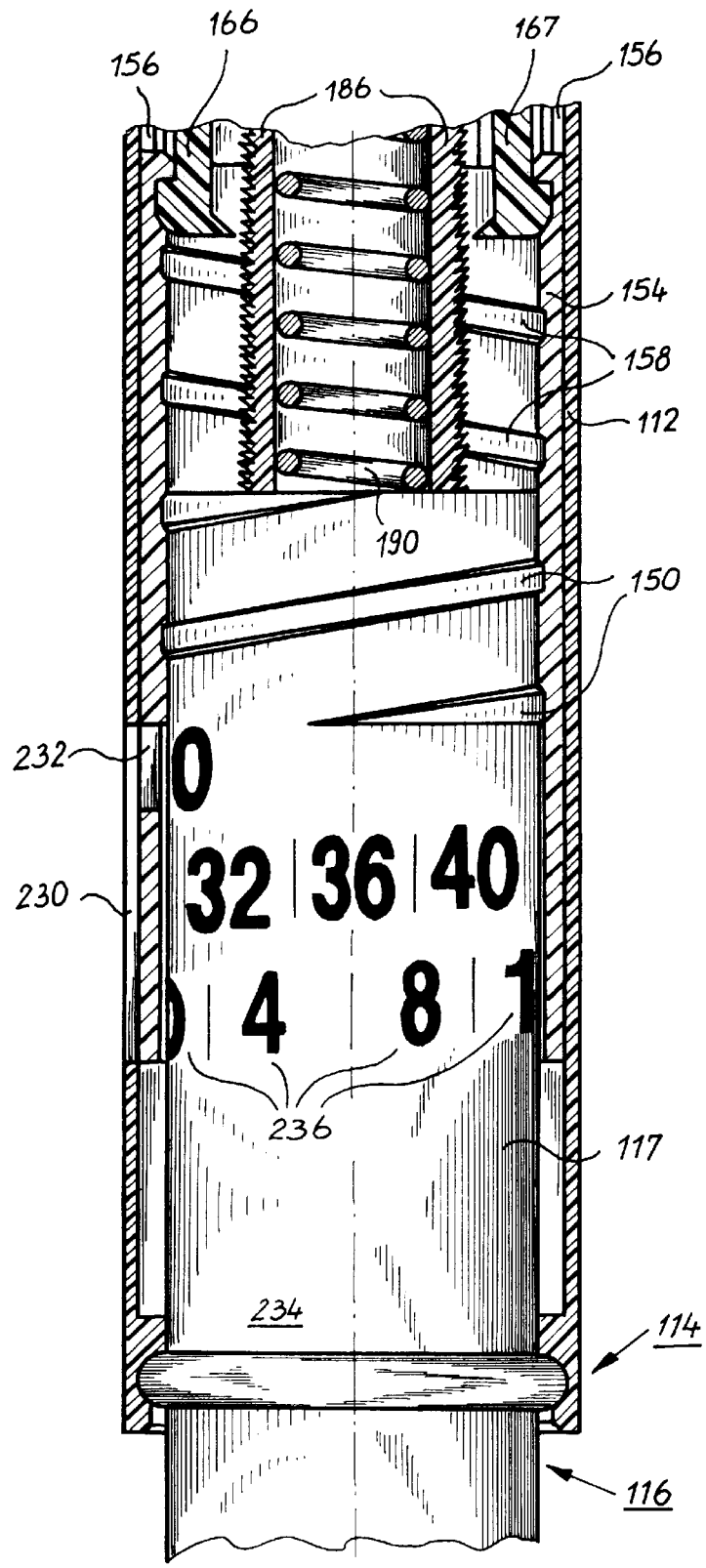
FIG. 21 is a view analogous to FIG. 20, but showing the maximum dose which can be selected.

FIGS. 20 & 21 show the parts of the injector which are provided for dose setting. The tubular section 116 is shown in both these figures in side view, i.e. not in section. It is rotatably mounted in housing 112 by bearing 114, so that it can be rotated in housing 112 without being axially displaced.

On its outer side, the portion 117 of tubular section 116 which is within housing 112 has an external thread 150 (coarse pitch thread) whose ridges have a preferably trapezoidal cross-section, and this external thread 150 engages in a corresponding internal thread 158 (FIG. 21) in the threaded sleeve 154 serving as a dosing element, which sleeve is axially guided in longitudinal grooves 156 of housing 112, and therefore cannot turn in housing 112, but only move axially.

Housing 112 has a longitudinal window 230, whose form is shown in FIG. 1, and which extends in the longitudinal direction of housing 112. It serves for indication of the selected injection dose.

Similarly, dosing element 154 has a window 232, which is axially shorter than window 230, but can have the same width. Further, on the outer side 234 of tubular section 116, there are, in the manner shown, display values 236 for the injection dose, i.e. here the numbers 0, 2, 4, . . . 60.

Window 232 is so dimensioned that, of these display values 236, only one at a time can be displayed, e.g., as shown in FIG. 1, the display value "60".

As one can see from FIGS. 20 & 21, the display values 236 are arranged in a screw or spiral pattern on the outer side 234 of part 117, i.e. with increasing dose, the display in window 230 "migrates" in the distal direction, since the threaded sleeve 154 is moving in the distal direction in housing 112.

FIG. 20 shows the position of dosing element 154 for the injection dose "0"; this position is also shown in FIG. 5. FIG. 21 shows the position of dosing element 154 for the maximum injection dose, thus e.g. "60"; this is also shown in FIG. 1. A comparison of FIGS. 20 & 21 shows the differing position of dosing element 154 relative to housing 112, and the differing position of window 232 relative to window 230.

It is again to be noted that a single dose selection in window 232, e.g. four insulin units ("4") is effective for all subsequent injections in the same manner, i.e. when this dose is maintained unchanged, a single setting or adjustment suffices, which for the patient represents a substantial simplification, since, given a constant dose, he need not concern himself about dose setting prior to an injection.

Naturally, within the scope of the present invention, many changes and modifications are possible, e.g. design of the injection device of the invention as a so-called "full automatic" injector with a fully automatic operation of the injection process.

What is claimed is:

1. An injection device, comprising
    a housing and a fluid container therein;
    an expressing member longitudinally movable within the housing for expressing injection fluid from said fluid container;
    an actuating member associated with the expressing member and longitudinally movable within said housing between a proximal and a distal end position for longitudinal displacement of said expressing member within said housing;
    a plunger disposed in said fluid container and axially aligned with said expressing member;
    and a position-dependent connecting means between said actuating member and said expressing member, said connecting means being disabled in said distal end position of said actuating member and enabled in a position range adjacent said distal end position and including said proximal end position of said actuating member;
    wherein the expressing member is biased in the proximal direction by a force, which is smaller than a detachment force of said plunger disposed in the fluid container, so that, when said actuating member is in said distal end position and said connecting means is disabled, said biasing force moves the expressing member into abutment with the plunger, without pushing the plunger into the fluid container; and further comprising
    a compression spring located between, and generating said biasing force between, said housing and said expressing member.

2. The injection device according to claim 1, wherein said expressing member is formed with an interior cavity, and said compression spring is disposed at least partially within said cavity inside said expressing member.

3. The injection device according to claim 2, wherein
    said cavity, formed in said expressing member, has an essentially cylindrical shape and thereby guides said compression spring.

4. The injection device according to claim 1, wherein said distal end position of said actuating member is defined by an adjustable stop.

5. The injection device according to claim 4, further comprising a dosing element arranged in the housing in a longitudinally movable but non-rotatable manner, said adjustable stop being formed on said dosing element.

6. The injection device according to claim 5, further comprising an adjusting element rotatable but not longitudinally movable within sad housing, and formed with a threaded surface, and wherein
    said dosing element comprising said stop is formed with a thread which engages a complementary thread on said adjusting element, so that rotation of said adjusting element relative to said housing moves said dosing element in a longitudinal direction of said housing.

7. The injection device according to claim 1, wherein a guide member having a tongue-and-grove sliding engagement with said expressing member for guiding same in the longitudinal direction relative to said housing.

8. The injection device according to claim 1, wherein said position-dependent connecting means, between said actuating member and said expressing member, includes a longitudinally extending series of indentations formed in said expressing member and at least one catch element provided on said actuating member for selective engagement into one of said indentations.

9. The injection device according to claim 8,
    wherein said indentations are arranged at an essentially equal interval (T) from each other.

10. The injection device according to claim 8, wherein at least one catch element is elastically biased away from said expressing member.

11. An infection device comprising
    a housing and a fluid container therein;
    an expressing member longitudinally movable within the housing for expressing injection fluid from said fluid container;
    an actuating member associated with the expressing member and longitudinally movable within said housing between a proximal and a distal end position for longitudinal displacement of said expressing member within said housing;
    a plunger disposed in said fluid container and axially aligned with said expressing member;
    and a position-dependent connector arranged between said actuating member and said expressing member, said connector being disabled in said distal end position of said actuating member and enabled in a position range adjacent said distal end position and including said proximal end position of said actuating member;
    wherein the expressing member is biased in the proximal direction by a force, which is smaller than a detachment force of said plunger disposed in the fluid container, so that, when said actuating member is in said distal end position and said connector is disabled, said biasing force moves the expressing member into abutment with the plunger, without pushing the plunger into the fluid container; and further comprising
    a dose-adjusting element rotatable but not longitudinally movable within said housing and formed with a thread on a surface thereof, and
    a dosing element arranged in the housing in a longitudinally movable but non-rotatable manner and formed with a thread engaging the thread of the dose-adjusting element, so that rotation of said adjusting element relative to the housing moves the dosing element in a longitudinal direction of the housing, said dosing element being provided with a stop defining the distal end position of the actuating member, said rotatably mounted adjusting element having, on its outer surface, indicia for the injection dose, one of said indicia, corresponding to a currently selected injection dose, being readable through a window structure which includes a first window provided in said housing and a second window provided in said dosing element having said stop.

12. The injection device according to claim 11, wherein said adjusting element, rotatably mounted in said housing is adapted to receive said fluid container filled with an injectable fluid.

13. The injection device according to claim 11, wherein said second window, formed in said dosing element having said stop, is so dimensioned that it corresponds to an area of a single indication value of said indicia and has a periphery covering and obscuring adjacent indication values.

14. The injection device according to claim 10, wherein said first window, formed in said housing, has the form of a longitudinal slot which extends essentially in a longitudinal direction of the injection device.

15. The injection device according to claim 11, further comprising a compression spring located between, and generating said biasing force between, said housing and said expressing member.

16. The injection device according to claim 11, wherein said expressing member is formed with an interior cavity, and said compression spring is disposed at least partially within said cavity inside said expressing member.

17. An injection device, comprising a housing and a fluid container therein;

an expressing member longitudinally movable within the housing for expressing injection fluid from said fluid container;

a plunger axially movable within said fluid container;

an actuating member associated with the expressing member and longitudinally movable within said housing between a proximal and a distal end position for longitudinal displacement of said expressing member within said housing;

and a position-dependent connecting means between said actuating member and said expressing member, said connecting means being disabled in said distal end position of said actuating member and enabled in a position range adjacent said distal end position and including said proximal end position of said actuating member;

wherein said position-dependent connecting means, between said actuating member and said expressing member, includes a longitudinally extending series of indentations formed in said expressing member and at least one catch element provided on said actuating member for selective engagement into one of said indentations; and wherein the position-dependent connecting means comprises a plurality of longitudinally extending series of equally-spaced indentations on an outer surface of the expressing member and a plurality of catch elements provided on said actuating member, and axial positions of at least one of said indentations and said catch elements are so dimensioned that, at any given relative position of said expressing member and said actuating member, at least one of said catch elements is not in full engagement with an indentation of an associated one of said series of indentations.

18. The injection device according to claim 17, wherein said at least one series of equally-spaced indentations is formed as a row of teeth.

19. The injection device according to claim 18, wherein said at least one catch element is sprung radially outward, and said cam control operates against the radial spring force of said catch element.

20. The injection device according to claim 19, wherein said separate rows of teeth are staggered in the axial direction by at least half a tooth interval with respect to each other.

21. An injection device, comprising a housing and a fluid container therein;

an expressing member longitudinally movable within the housing for expressing injection fluid from said fluid container;

an actuating member associated with the expressing member and longitudinally movable within said housing between a proximal and a distal end position for longitudinal displacement of said expressing member within said housing;

a plunger disposed in said fluid container and axially aligned with said expressing member;

and a position-dependent connector arranged between said actuating member and said expressing member, said connector being disabled in said distal end position of said actuating member and enabled in a position range adjacent said distal end position and including said proximal end position of said actuating member;

wherein the expressing member is biased in the proximal direction by a force, which is smaller than a detachment force of said plunger disposed in the fluid container, so that, when said actuating member is in said distal end position and said connector is disabled, said biasing force moves the expressing member into abutment with the plunger, without pushing the plunger into the fluid container, said position-dependent connector comprising a longitudinally extending series of indentations formed in said expressing member and at least one catch element provided on said actuating member for selective engagement into one of said indentation, and a cam control associated with said at least one catch element and controlling the position thereof, relative to the expressing member, as a function of the axial position of said actuating member.

22. The injection device according to claim 21, wherein said at least one catch element is sprung radially outward, and said cam control operates against the radial spring force of said catch element.

23. The injection device according to claim 21, wherein said at least one catch element has a radial outer surface which is formed with a cam surface and a counter-cam surface is provided on said housing, said cam surface and said counter-cam surface interacting with each other, thereby serving as said cam control.

24. The injection device according to claim 21, wherein said at least one catch element is adapted for form-locking engagement with an associated indentation.

25. The injection device according to claim 21, wherein said expressing member is formed with an interior cavity and a compression spring is disposed at least partially within said cavity inside said expressing member.

* * * * *

UNITED STATES PATENT AND TRADEMARK OFFICE
CERTIFICATE OF CORRECTION

PATENT NO. : 6,048,336
DATED : April 11, 2000
INVENTOR(S) : Gabriel

It is certified that error appears in the above-indentified patent and that said Letters Patent is hereby corrected as shown below:

ON THE TITLE PAGE, ITEM :

[56] References Cited

U.S. PATENT DOCUMENTS

--4,710,178   12/1987   Leonard et al.........604/209
should be added.--

--5,433,352   7/1995   Ronvig................222/391
should be added.--

--5,599,314   2/1997   Neill.................604/207

UNITED STATES PATENT AND TRADEMARK OFFICE
CERTIFICATE OF CORRECTION

PATENT NO. : 6,048,336
DATED : April 11, 2000
INVENTOR(S) : Gabriel

Page 2 of 3

It is certified that error appears in the above-indentified patent and that said Letters Patent is hereby corrected as shown below:

FOREIGN PATENT DOCUMENTS
--WO 89-07463 A1  8/1989  Holm................ should be added.--

--EP 0 498 737 A1  8/1992  Saiki............... should be added.--

--DE 195 19 147 A1 12/1995  Bechtold & Gabriel.... should be added.--

--WO 96-03170 A1  2/1996  Bertschi & Zaugg....... should be added.--

UNITED STATES PATENT AND TRADEMARK OFFICE
CERTIFICATE OF CORRECTION

PATENT NO. : 6,048,336
DATED : April 11, 2000
INVENTOR(S) : Gabriel

It is certified that error appears in the above-indentified patent and that said Letters Patent is hereby corrected as shown below:

At column 7, claim 6, line 3 "sad" should be --said--.

At column 7, claim 7, line 2 "grove" should be --groove--.

At column 8, claim 11, line 1 "infection" should be --injection--.

Signed and Sealed this

Thirteenth Day of March, 2001

Attest:

NICHOLAS P. GODICI

Attesting Officer

Acting Director of the United States Patent and Trademark Office